US011971467B2

(12) United States Patent
Huang et al.

(10) Patent No.: US 11,971,467 B2
(45) Date of Patent: Apr. 30, 2024

(54) FREE-BREATHING ABDOMINAL MAGNETIC RESONANCE FINGERPRINTING USING A PILOT TONE NAVIGATOR

(71) Applicant: Case Western Reserve University, Cleveland, OH (US)

(72) Inventors: Sherry Huang, Cleveland Heights, OH (US); Mark Griswold, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 85 days.

(21) Appl. No.: 17/905,923

(22) PCT Filed: Mar. 15, 2021

(86) PCT No.: PCT/US2021/022305
§ 371 (c)(1),
(2) Date: Sep. 8, 2022

(87) PCT Pub. No.: WO2021/183989
PCT Pub. Date: Sep. 16, 2021

(65) Prior Publication Data
US 2023/0176156 A1 Jun. 8, 2023

Related U.S. Application Data

(60) Provisional application No. 62/989,183, filed on Mar. 13, 2020.

(51) Int. Cl.
G01R 33/56 (2006.01)
A61B 5/055 (2006.01)
(Continued)

(52) U.S. Cl.
CPC .......... *G01R 33/5673* (2013.01); *A61B 5/055* (2013.01); *A61B 5/08* (2013.01); *G01R 33/385* (2013.01)

(58) Field of Classification Search
CPC .. G01R 33/5673; G01R 33/385; G01R 33/50; G01R 33/561; A61B 5/055; A61B 5/08
See application file for complete search history.

(56) References Cited

U.S. PATENT DOCUMENTS 8,723,518 B2    5/2014  Seiberlich et al.
2015/0301141 A1 10/2015 Griswold et al.
(Continued)

OTHER PUBLICATIONS

Ludwig et al. Pilot tone-based motion correction for prospective respiratory compensated cardiac cine MRI Magn Reson Med. 2021;85:2403-2416. (Year: 2021).*
(Continued)

*Primary Examiner* — G. M. A Hyder
(74) *Attorney, Agent, or Firm* — Quarles & Brady LLP

(57) ABSTRACT

A method for free-breathing abdominal magnetic resonance fingerprinting (MRF) includes applying a pilot tone (PT) RF signal in an MRI system environment using a PT RF signal source, acquiring MRF data from a region of interest in subject using free-breathing MRF pulse sequence and acquiring PT navigator signals based on the applied PT RF signal. The PT navigator signals are associated with a plurality of respiratory states and are encoded with acquired MRF data. The method further includes generating images for each of the plurality of respiratory states based on MRF data and the PT navigator signals. For each respiratory state, the generated images for the respiratory state are compared to a respiratory state MRF dictionary associated with the respiratory state to determine tissue property of the MRF data associated with the respiratory state. A quantitative (Continued)

parameter map may be generated for the determined tissue properties for each respiratory state.

20 Claims, 6 Drawing Sheets

(51) Int. Cl.
  *A61B 5/08* (2006.01)
  *G01R 33/385* (2006.01)
  *G01R 33/567* (2006.01)

(56) References Cited

U.S. PATENT DOCUMENTS

| | | | |
|---|---|---|---|
| 2016/0091591 A1* | 3/2016 | Grodzki | G01R 33/56509 324/309 |
| 2017/0319098 A1 | 11/2017 | Wang et al. | |
| 2018/0217220 A1 | 8/2018 | Gulani et al. | |
| 2019/0377051 A1 | 12/2019 | Bacher et al. | |

OTHER PUBLICATIONS

Chen, Yong et al. "Magnetic resonance fingerprinting (MRF) for rapid quantitative abdominal imaging." In Proceedings of the 22nd Annual Meeting of ISMRM, Milan, Italy, vol. 22, p. 561. 2014.
Chen, Yong et al. "Free-breathing 3D abdominal magnetic resonance fingerprinting using navigators." In Proc Intl Soc Mag Reson Med, vol. 24. 2016.
Schroeder, Lea et al. "Two-dimensional respiratory-motion characterization for continuous MR measurements using pilot tone navigation." In Proceedings of the 24th Annual Meeting of ISMRM, Singapore, p. 3103. 2016.
Speier, P. et al. "PT-Nav: a novel respiratory navigation method for continuous acquisitions based on modulation of a pilot tone in the MR-receiver." Magn Reson Mater Phys Biol Med 28 (2015): S97-S98.
Ludwig, Juliane et al. "Pilot tone-based prospective respiratory motion correction for 2D cine cardiac MRI." Pilot tone-based prospect respir motion correct 2D cine card MRI 27 (2019): 73.
Ma, Dan et al. "Magnetic resonance fingerprinting." Nature 495, No. 7440 (2013): 187-192.
Chen, Yong et al. "Three-dimensional MR fingerprinting for quantitative breast imaging." Radiology 290, No. 1 (2019): 33.
McGivney, Debra F. et al. "SVD compression for magnetic resonance fingerprinting in the time domain." IEEE transactions on medical imaging 33, No. 12 (2014): 2311-2322.
De Bazelaire, Cedric MJ et al. "MR imaging relaxation times of abdominal and pelvic tissues measured in vivo at 3.0 T: preliminary results." Radiology 230, No. 3 (2004): 652-659.
Chen, Yong et al. "Rapid volumetric T1 mapping of the abdomen using three-dimensional through-time spiral GRAPPA." Magnetic resonance in medicine 75, No. 4 (2016): 1457-1465.
Stanisz, Greg J. et al. "T1, T2 relaxation and magnetization transfer in tissue at 3T." Magnetic Resonance in Medicine: An Official Journal of the International Society for Magnetic Resonance in Medicine 54, No. 3 (2005): 507-512.
Ma, Dan et al. "Fast 3D magnetic resonance fingerprinting for a whole-brain coverage." Magnetic resonance in medicine 79, No. 4 (2018): 2190-2197.
Liao, Congyu et al. "3D MR fingerprinting with accelerated stack-of-spirals and hybrid sliding-window and GRAPPA reconstruction." Neuroimage 162 (2017): 13-22.
Gallichan, Daniel et al. "Retrospective correction of involuntary microscopic head movement using highly accelerated fat image navigators (3D FatNavs) at 7T." Magnetic resonance in medicine 75, No. 3 (2016): 1030-1039.
Seiberlich, Nicole et al. "Improved temporal resolution in cardiac imaging using through-time spiral GRAPPA." Magnetic resonance in medicine 66, No. 6 (2011): 1682-1688.
Chen, Yong et al. "Free-breathing liver perfusion imaging using 3D through-time spiral GRAPPA acceleration." Investigative radiology 50, No. 6 (2015): 367.
PCT International Search Report from PCT/US2021/022305.
Deng, Jie, and Andrew C. Larson. "Modified Propeller approach for T2-mapping of the abdomen." Magnetic Resonance in Medicine: An Official Journal of the International Society for Magnetic Resonance in Medicine 61.6 (2009): 1269-1278.
Kim, Kyung Ah, et al. "Quantitative evaluation of liver cirrhosis using T1 relaxation time with 3 tesla MRI before and after oxygen inhalation." Journal of Magnetic Resonance Imaging 36.2 (2012): 405-410.
Hueper, Katja, et al. "T1-mapping for assessment of ischemia-induced acute kidney injury and prediction of chronic kidney disease in mice." European radiology 24 (2014): 2252-2260.
Peperhove, Matti, et al. "Assessment of acute kidney injury with T1 mapping MRI following solid organ transplantation." European radiology 28 (2018): 44-50.
Wolf, Marcos, et al. "Magnetic resonance imaging T1-and T2-mapping to assess renal structure and function: a systematic review and statement paper." Nephrology Dialysis Transplantation 33.suppl_2 (2018): ii41-ii50.
Wang, Charlie Yi, et al. "Magnetic resonance fingerprinting with quadratic RF phase for measurement of T2* simultaneously with δf, T1, and T2." Magnetic resonance in medicine 81.3 (2019): 1849-1862.
Benjamin, Henninger, et al. "Evaluation of liver fat in the presence of iron with MRI using T2* correction: a clinical approach." European radiology 23 (2013): 1643-1649.
Deshmane, Anagha, et al. "Partial volume mapping using magnetic resonance fingerprinting." NMR in Biomedicine 32.5 (2019): e4082.
Yang, Mingrui, et al. "Low rank approximation methods for MR fingerprinting with large scale dictionaries." Magnetic resonance in medicine 79.4 (2018): 2392-2400.
McGivney, Debra, et al. "Towards continuous dictionary resolution in MR fingerprinting using a quadratic inner product model." Proceedings of the 25th Annual Meeting of ISMRM, Montréal, QC, Canada. vol. 27. 2019.
Hamilton, Jesse I., et al. "Simultaneous multislice cardiac magnetic resonance fingerprinting using low rank reconstruction." NMR in Biomedicine 32.2 (2019): e4041.
Franke, Mareike, et al. "Magnetic resonance T2 mapping and diffusion-weighted imaging for early detection of cystogenesis and response to therapy in a mouse model of polycystic kidney disease." Kidney international 92.6 (2017): 1544-1554.
Kaltwasser, J. P., et al. "Non-invasive quantitation of liver iron-overload by magnetic resonance imaging." British journal of haematology 74.3 (1990): 360-363.
Catalano, Onofrio A., et al. "Comparison of the clinical performance of upper abdominal PET/DCE-MRI with and without concurrent respiratory motion correction (MoCo)." European Journal of Nuclear Medicine and Molecular Imaging 45 (2018): 2147-2154.
Shah, Bhavya, et al. "Quantitative MR imaging: physical principles and sequence design in abdominal imaging." Radiographics 31.3 (2011): 867-880.
Hamilton, Jesse I., et al. "MR fingerprinting for rapid quantification of myocardial T1, T2, and proton spin density." Magnetic resonance in medicine 77.4 (2017): 1446-1458.
Jiang, Yun, et al. "MR fingerprinting using fast imaging with steady state precession (FISP) with spiral readout." Magnetic resonance in medicine 74.6 (2015): 1621-1631.
Vahle, Thomas, et al. "Respiratory motion detection and correction for MR using the pilot tone: applications for MR and simultaneous PET/MR exams." Investigative radiology 55.3 (2020): 153.
Rigie, David, et al. "Tracking Respiratory Motion Throughout Arbitrary MRI Sequences via Pilot Tone Navigation." Proceedings of the International Society for Magnetic Resonance in Medicine.
Luetkens, Julian A., et al. "Quantification of liver fibrosis at T1 and T2 mapping with extracellular volume fraction MRI: preclinical results." Radiology 288.3 (2018): 748-754.
Hoffman, David H., et al. "MR elastography, T1 and T2 relaxometry of liver: role in noninvasive assessment of liver function and portal hypertension." Abdominal Radiology 45 (2020): 2680-2687.

(56) References Cited

OTHER PUBLICATIONS

Hoffman, David H., et al. "T1 mapping, T2 mapping and MR elastography of the liver for detection and staging of liver fibrosis." Abdominal Radiology 45 (2020): 692-700.

Dekkers, Ilona A., et al. "Consensus-based technical recommendations for clinical translation of renal T1 and T2 mapping MRI." Magnetic Resonance Materials in Physics, Biology and Medicine 33 (2020): 163-176.

Tirkes, Temel, et al. "T1 mapping for diagnosis of mild chronic pancreatitis." Journal of Magnetic Resonance Imaging 45.4 (2017): 1171-1176.

Wang, Min, et al. "Magnetic resonance elastography and T1 mapping for early diagnosis and classification of chronic pancreatitis." Journal of Magnetic Resonance Imaging 48.3 (2018): 837-845.

Wang, Wen-Tao, et al. "T1 mapping on gadoxetic acid-enhanced MR imaging predicts recurrence of hepatocellular carcinoma after hepatectomy." European Journal of Radiology 103 (2018): 25-31.

Adams, Lisa C., et al. "Use of quantitative T2 mapping for the assessment of renal cell carcinomas: first results." Cancer Imaging 19 (2019): 1-11.

Xu, Zhongbiao, et al. "Rigid motion correction for magnetic resonance fingerprinting with sliding-window reconstruction and image registration." Magnetic resonance imaging 57 (2019): 303-312.

Zhu, Xucheng, et al. "Iterative motion-compensation reconstruction ultra-short TE (iMoCo UTE) for high-resolution free-breathing pulmonary MRI." Magnetic resonance in medicine 83.4 (2020): 1208-1221.

\* cited by examiner

FREE-BREATHING ABDOMINAL MAGNETIC RESONANCE FINGERPRINTING USING A PILOT TONE NAVIGATOR

CROSS-REFERENCE TO RELATED APPLICATIONS

This application represents the U.S. national stage of PCT/US2021/022305, filed Mar. 15, 2021, which is based on, and claims priority to, U.S. Ser. No. 62/989,183, filed Mar. 13, 2020, each of which are incorporated by reference in their entireties.

BACKGROUND

Current clinical abdominal magnetic resonance imaging (MM) routine protocols rely on qualitative imaging with contrast weighted images as the main diagnostic tool. While these images can provide information about tissue characteristics, they require interpretations of signal intensities that are not well standardized and can thus induce bias and errors. On the other hand, quantitative mapping in MM provides fundamental properties of the tissues under investigation. Typical quantitative measurements include, for example, proton density ($M_0$), $T_1$ relaxation time, and $T_2$ relaxation time. In the abdomen, quantitative mapping can provide valuable insights into diseased and healthy tissue characterization for various clinical applications, such as lesion detection, cirrhotic liver tissue differentiation, assessment of kidney injury and functions, and iron quantification.

Quantitative $T_1$ and $T_2$ mapping of the abdomen, however, can be immensely challenging. Respiratory motion can introduce artifacts such as blurring and ghosting in the resulting images of the abdomen. To prevent this issue, most sequences for quantitative imaging of the abdomen are performed with the breath-holds, however, image degradation still occurs from residual motion. Furthermore, certain patient populations have difficulties in following breathing instructions for breath-holds. In addition, traditional quantitative mapping methods are time-consuming and inefficient because multiple contrast weighted images (and multiple acquisitions) are often needed to generate a single quantitative map. Conventionally, each sequence is only able to provide a single tissue property map and thus multiple acquisitions are often needed to obtain various quantitative measures. These separate acquisitions are not typically co-registered to each other, which introduces additional variability from subject motion in between acquisitions. Therefore, even though there are potential benefits of quantitative imaging, qualitative imaging remains the clinical standard.

Magnetic resonance fingerprinting (MRF) is a relatively new framework for fast quantitative MR imaging that allows for simultaneous quantification of multiple tissue properties, such as $T_1$, $T_2$, and $M_0$, in different regions of the body. Previous studies have shown that MRF can provide simultaneous $T_1$, $T_2$, and $M_0$ quantifications in a single breath-hold for two-dimensional abdominal imaging. The previous MRF method for abdominal imaging allows quantification of tissues with higher efficiency than traditional approaches. However, the use of abdominal MRF for tissue characterization has been hindered by the requirement for breath-holds. As mentioned above, breath-holds can be difficult for certain populations. In addition, a clinical application that favors three-dimensional volumetric coverage of the abdomen is difficult to accomplish due to respiratory motion.

It would be desirable to provide a system and method for free-breathing quantitative MRF imaging that overcomes the aforementioned drawbacks.

SUMMARY OF THE DISCLOSURE

In accordance with an embodiment, a method for free-breathing abdominal magnetic resonance fingerprinting (MRF) includes applying a pilot tone (PT) radiofrequency (RF) signal in a magnetic resonance imaging (MM) system environment using a PT RF signal source and acquiring, using the MRI system, MRF data from a region of interest in a subject using a free-breathing MRF pulse sequence. The method further includes acquiring, using the MM system, PT navigator signals based on the applied PT RF signal. The PT navigator signals are associated with a plurality of respiratory states and the PT navigator signals are encoded with the acquired MRF data. The method further includes generating, using a processor, one or more images for each of the plurality of respiratory states based on the MRF data and the PT navigator signals and for each respiratory state, comparing the one or more images for the respiratory state to a respiratory state MRF dictionary associated with the respiratory state to determine at least one tissue property of the MRF data associated with the respiratory state. The method further includes generating at least one quantitative parameter map for the at least one tissue property for each respiratory state.

In accordance with another embodiment, a system for generating quantitative maps for a region of interest in a subject includes a pilot tone (PT) radiofrequency (RF) signal source configured to generate a PT RF signal and a magnetic resonance imaging (MRI) system. The MRI system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array and a computer system. The computer system is programmed to acquire MRF data from a region of interest in a subject using the MRI system and a free-breathing MRF pulse sequence and acquire PT navigator signals based on the applied PT RF signal using the MM system. The PT navigator signals are associated with a plurality of respiratory states the PT navigator signals are encoded with the acquired MRF data. The computer system is further programed to generate one or more images for each of the plurality of respiratory states based on the MRF data and the PT navigator signals and for each respiratory state, compare the one or more images for the respiratory state to a respiratory state MRF dictionary associated with the respiratory state to determine at least one tissue property of the MRF data associated with the respiratory state. The computer system is further programmed to generate at least one quantitative parameter map for the at least one tissue property for each respiratory state.

BRIEF DESCRIPTION OF THE DRAWINGS

The present invention will hereafter be described with reference to the accompanying drawings, wherein like reference numerals denote like elements.

DETAILED DESCRIPTION

Figure 1:
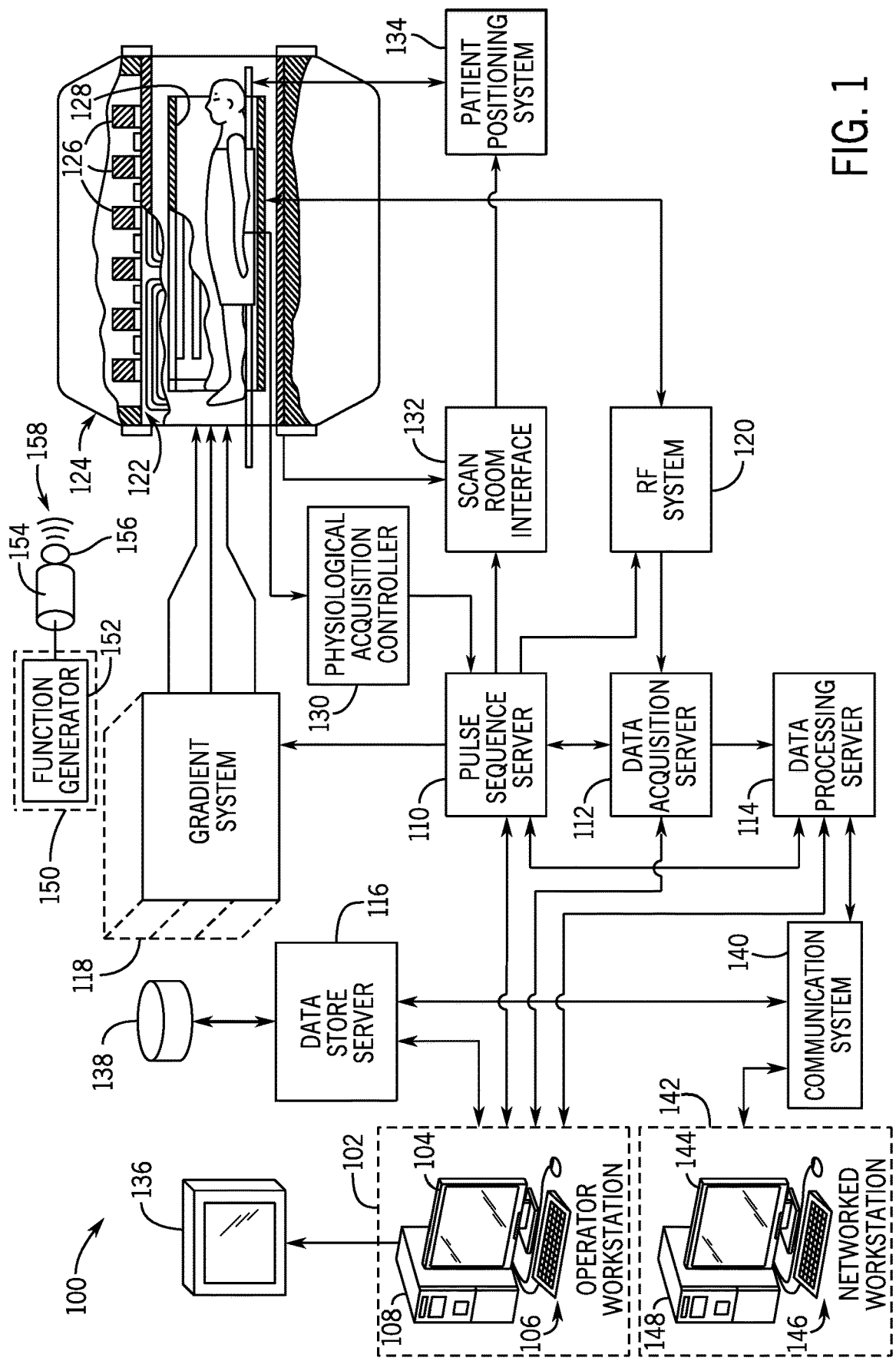
FIG. 1 is a schematic diagram of an MRI system with a pilot tone (PT) navigator in accordance with an embodiment.

Magnetic resonance fingerprinting ("MRF") is a technique that facilitates mapping of tissue or other material properties based on random or pseudorandom measurements of the subject or object being imaged. In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE'), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, tissue parameters or properties such as longitudinal relaxation time ($T_1$), transverse relaxation time ($T_2$), and proton density ($\rho$), and device dependent parameters such as main or static magnetic field map ($B_0$). MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; R(G) is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation differences; and $M_0$ is the magnetization in the default or natural alignment to which spins align when placed in the main magnetic field.

While $E_i(T_1,T_2,D)$ is provided as an example, in different situations, the decay term, $E_i(T_1,T_2,D)$, may also include additional terms, $E_i(T_1,T_2,D, \ldots)$ or may include fewer terms, such as by not including the diffusion relaxation, as $E_i(T_1,T_2)$ or $E_i(T_1,T_2, \ldots)$. Also, the summation on "j" could be replace by a product on "j". The dictionary may store signals described by, $$S_i = R_i E_i(S_{i-1}) \quad (2);$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

Thus, in MRF, a unique signal timecourse is generated for each pixel. This timecourse evolves based on both physiological tissue properties such as T1 or T2 as well as acquisition parameters like flip angle (FA) and repetition time (TR). This signal timecourse can, thus, be referred to as a signal evolution and each pixel can be matched to an entry in the dictionary, which is a collection of possible signal evolutions or timecourses calculated using a range of possible tissue property values and knowledge of the quantum physics that govern the signal evolution. Upon matching the measured signal evolution/timecourse to a specific dictionary entry, the tissue properties corresponding to that dictionary entry can be identified. A fundamental criterion in MRF is that spatial incoherence be maintained to help separate signals that are mixed due to undersampling. In other words, signals from various locations should differ from each other, in order to be able to separate them when aliased.

To achieve this process, a magnetic resonance imaging (MRI) system or nuclear magnetic resonance (NMR) system may be utilized. FIG. 1 shows an MRI system 100 that may be used to perform magnetic resonance fingerprinting. In addition, MM system 100 may be used to implement the methods described herein. MM system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MM system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MM pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (3);$$

and the phase of the received magnetic resonance signal may also be determined according to the following relationship:

$$\varphi = \tan^{-1}\left(\frac{Q}{I}\right). \qquad (4)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MM system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure describes a system and method for a free-breathing imaging technique which integrates pilot tone (PT) navigator and magnetic resonance fingerprinting (MRF) to provide simultaneous quantification of multiple tissue properties in the abdomen in a plurality of respiratory states or phases (e.g., end-inhalation and end-exhalation states of the respiratory motion) using retrospective or prospective gating of respiratory motion. In various embodiments, the quantified tissue properties may include, for example, $T_1$, $T_2$, $T_2^*$, $M_0$, fat fraction (FF), water fraction (WF), and off-resonance. The system and method may be implemented with both two-dimensional (2D) and three-dimensional (3D) MRF acquisitions. The acquisitions may use MRF pulse sequences including, but not limited to, fast imaging with steady-state free precession (FISP) and quadratic RF phase-based magnetic resonance fingerprinting (qRF-MRF).

The described system and method advantageously increases the clinical feasibility of, for example, volumetric quantitative mapping in the abdomen. An advantage of the technique compared to traditional navigator approaches is the high temporal resolution of the PT signal. The self-navigated PT navigator MRF technique provides high temporal resolution for tracking of respiratory motion with two- and three-dimensional coverage of the abdomen enabling simultaneous quantification of multiple tissue properties during free-breathing. The disclosed PT navigator MRF technique may be used to provide multi-property mapping to diagnose and characterize disease throughout the abdomen using a completely free-breathing acquisition. For example, $T_1$ and $T_2$ mapping may be used to quantify liver fibrosis and to predict patient outcomes. $T_1$ and $T_2$ mapping has also been shown to highly correlate with MR elastography in measuring liver stiffness. Outside of the liver, $T_1$ and $T_2$ mapping has been shown to help guide clinical decisions in predicting clinical outcomes in parenchymal renal disease, kidney fibrosis, and cyst progression. $T_1$ mapping has also been shown to complement diagnosis of early chronic pancreatitis. In addition, in already identified lesions, $T_1$ and $T_2$ values can be used as reliable biomarkers in prediction of cancer nodule progressions in various organs. Abdominal T2* mapping would allow disease characterization such as iron deposits, microbleeds, and liver fibrosis. The disclosed free-breathing PT navigator MRF technique would allow for simultaneous quantification of all relevant maps in the abdomen using a single free-breathing acquisition with no additional patient setup.

Referring again to FIG. 1, a source 150 for providing a PT radiofrequency (RF) signal 158 for the PT navigator during an acquisition is located within an environment (e.g., a scanner room or MR suite) of the MRI system 100. In an embodiment, the PT RF signal source 150 is a function generator 152 used to generate the PT RF signal 158 and the function generator 152 may be synchronized to a clock of the MRI system (e.g., a 10 MHz clock). The PT RF signal source 150 may be coupled to, for example, a wave guide 154 and an antenna 156 (e.g., a loop antenna) to transmit the PT RF signal 158 into the MRI system 100 environment. In an embodiment, the PR RF signal 158 is a constant RF signal and has a frequency set to be outside the region of interest at the edge of the imaging field of view (FOV) for the MRF acquisition. The PT RF signal 158 is used to track and encode physiological motion (e.g., respiratory motion) and varies corresponding to the physiological motion. During an acquisition, the PT RF signal is picked up by the RF system 120 (e.g., the receiver channels or receiver arrays) and encoded (or embedded) into the MRF data acquired by the RF system 120 in response to an applied MRF pulse sequence. Accordingly, both the PT RF signal 158 and the MRF data may be acquired simultaneously during the acquisition. In an embodiment, the PT RF signal 158 may be played out continuously during the entire duration of an acquisition.

Figure 2A:
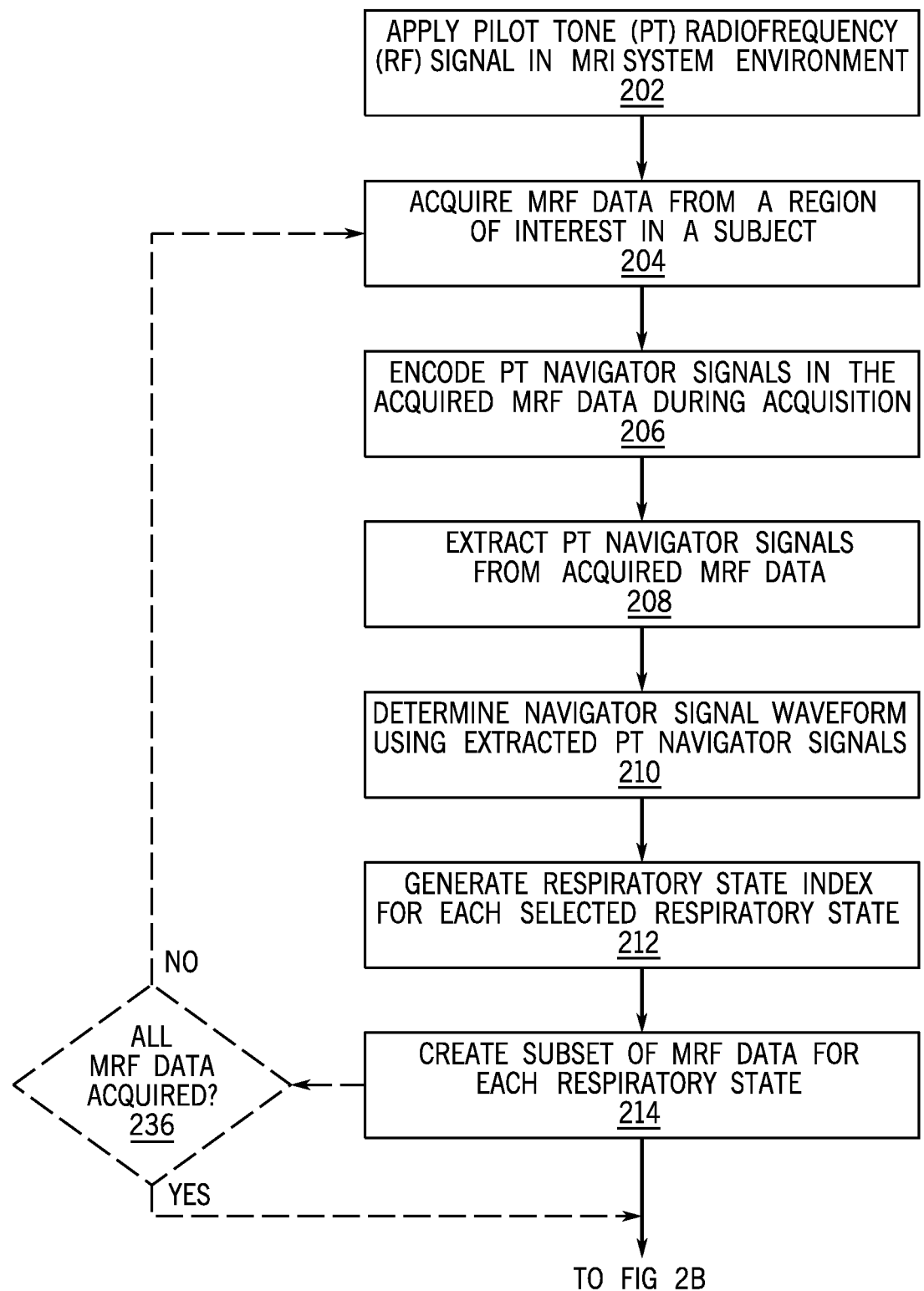
FIGS. 2A and 2B illustrate a method for free-breathing abdominal magnetic resonance fingerprinting (MRF) using a PT navigator in accordance with an embodiment.
Figure 2B:
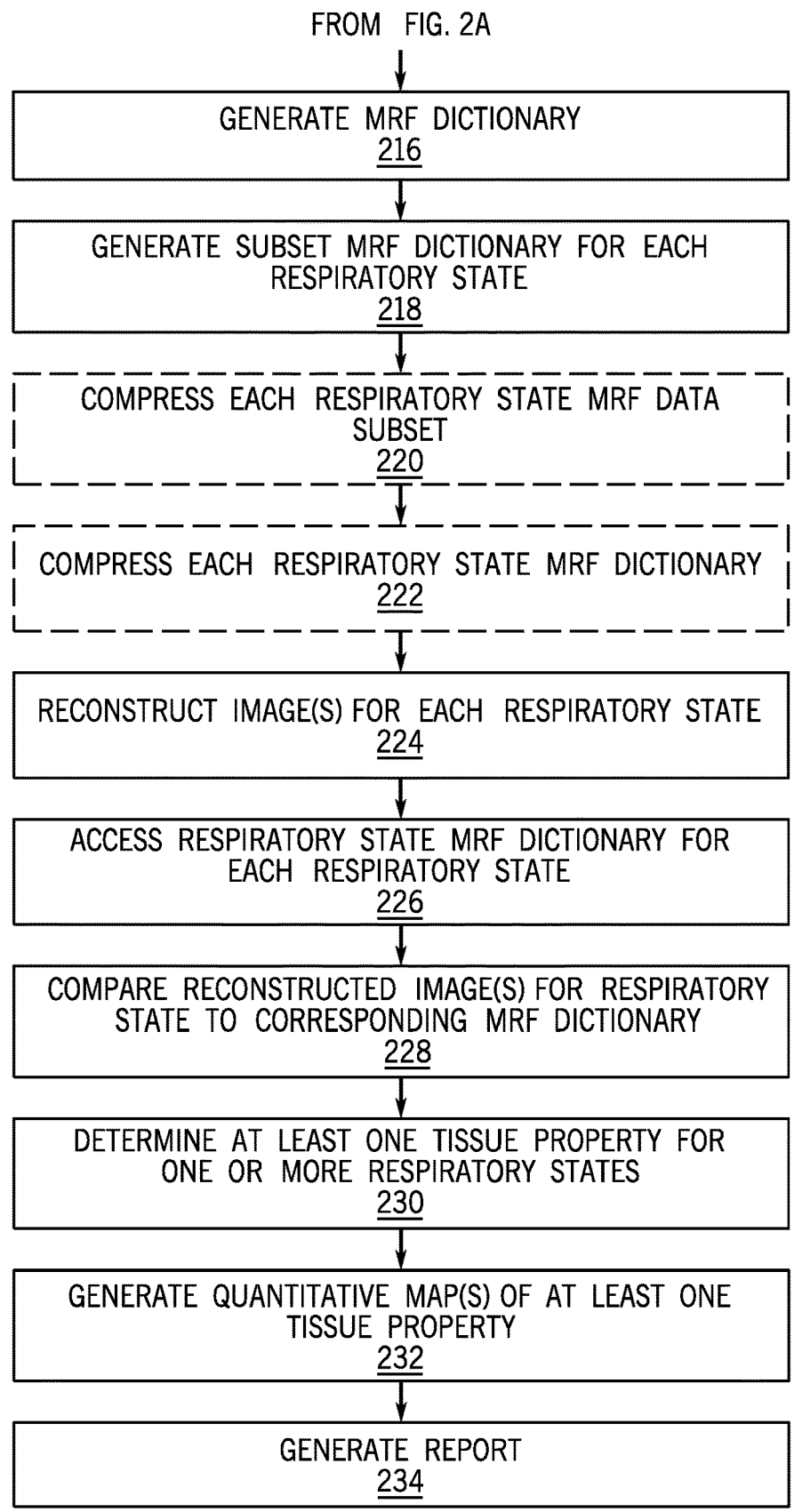

FIGS. 2a and 2b illustrate a method for free-breathing abdominal magnetic resonance fingerprinting (MRF) using a PT navigator in accordance with an embodiment. At block 202, a pilot tone (PT) radiofrequency (RF) signal is applied to an environment (e.g., a scanner room) of an MRI system (e.g., MRI system 100 shown in FIG. 1). For example, as discussed above a PT RF signal source may be used to apply (or transmit) the PT RF signal into the MRI system environment. In an embodiment, the PR RF signal is a constant RF signal and has a frequency set to be outside the region of interest at the edge of the imaging field of view (FOV). As mentioned above, the PT RF signal is used to track and encode physiological motion (e.g., respiratory motion) and varies corresponding to the physiological motion. In an embodiment, the PT RF signal may be played out continuously during the entire duration of an acquisition.

At block 204, MRF data is acquired from tissue in a region of interest (e.g., the abdomen) in a subject during free-breathing using an MRI system (e.g., MRI system 100 shown in FIG. 1). As discussed above, acquiring MRF data may include, for example, performing a pulse sequence using a series of varied sequence blocks to elicit a series of signal evolutions from the tissue in the subject. The MRF data may be acquired with two-dimensional (2D) or three-dimensional (3D) MRF acquisitions. In an embodiment, MRF data acquired with a 2D MRF acquisition may have the dimensions of number of readout points in each TR (Ns), the number of receive coils used (Nc), and the number of undersampled images or the number of TRs ($N_{images}$). In another embodiment, MRF data acquired with a 3D MRF acquisition may have the dimensions of number of readout points in each TR (Ns), the number of coils used (Nc), the number of undersampled images or the number of TRs ($N_{images}$), and the number of partitions acquired (Npart). In an embodiment, the temporal resolution of the applied PT RF signal may be set by the repetition time (TR) in the MRF pulse sequence used to acquire MRF data from the subject. Both the PT RF signal and the MR data may be detected and received simultaneously during the acquisition by a receiver array of the MR system (e.g., RF system 120 shown in FIG. 1). In an embodiment where retrospective gating is used, at block 204 all of the necessary MRF data is acquired using a predetermined number of measurements or acquisitions (for example, ten measurements or acquisitions for a 2D sequence or four measurements or acquisitions for a 3D sequence). In an embodiment where prospective gating is used, at block 204 MRF data is acquired using a single measurement or acquisition. As discussed further below, for prospective gating, the process of blocks 204 to 214 are repeated to acquire additional measurements until all the necessary MRF data is acquired.

Figure 3:
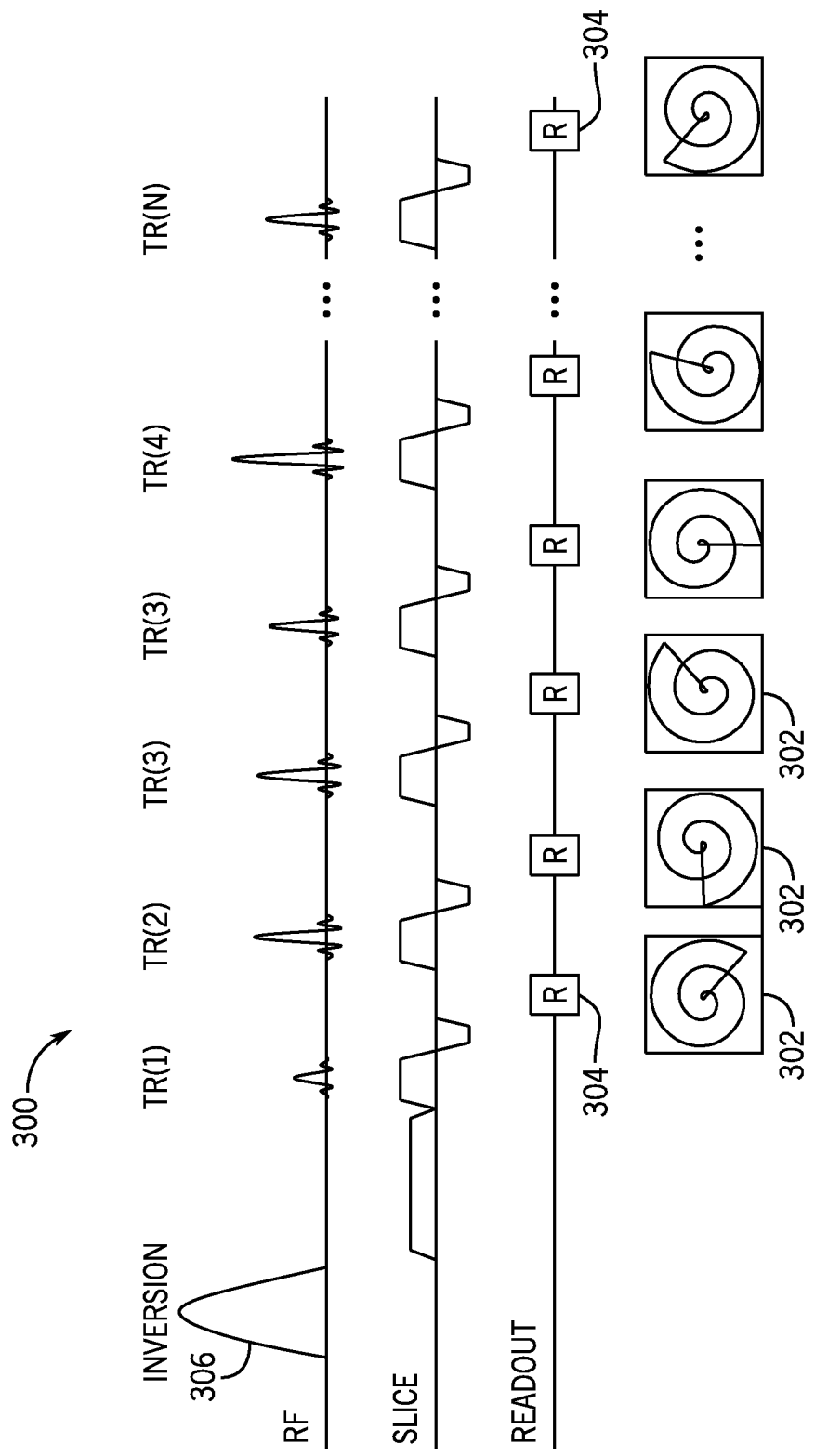
FIG. 3 illustrates an example two-dimensional (2D) FISP pulse sequence in accordance with an embodiment.

The MRF data is acquired during free-breathing of the subject and may be acquired using an MRF pulse sequence for abdominal imaging such as, for example, FISP, qRF-MRF, etc. FIG. 3 illustrates an example two-dimensional (2D) FISP pulse sequence in accordance with an embodiment. The 2D FISP sequence 300 shown in FIG. 3 utilizes a spiral MRF acquisition. In the FISP sequence 300, each time point may be acquired with a single spiral arm 302 during an acquisition window R 304 in one TR, which generates an undersampled image. For each 2D MRF measurement, a plurality of time points (e.g., hundreds) may be acquired using continuously varying sequence acquisition parameters such as flip angle and spiral trajectories with a golden-angle order. The FISP sequence 300 contains multiple inversion recovery 306 (e.g., n=3) modules to increase the sensitivity to the $T_1$ relaxation time. In an embodiment, the FISP sequence 300 may also include $T_2$-preparation modules (not shown), for example, n=6, to increase sensitivity to the $T_2$ relaxation time. In an embodiment, spectrally-selective fat suppression modules (not shown) may also be applied to suppress fat signal. In another embodiment, two-dimensional coronal acquisitions may be performed using FISP sequence 300 to better visualize respiratory motion. In an example, for each imaging slice in the coronal view, a plurality of measurements may be acquired and a waiting period applied in between each measurement to ensure signals are fully relaxed.

Figure 4:
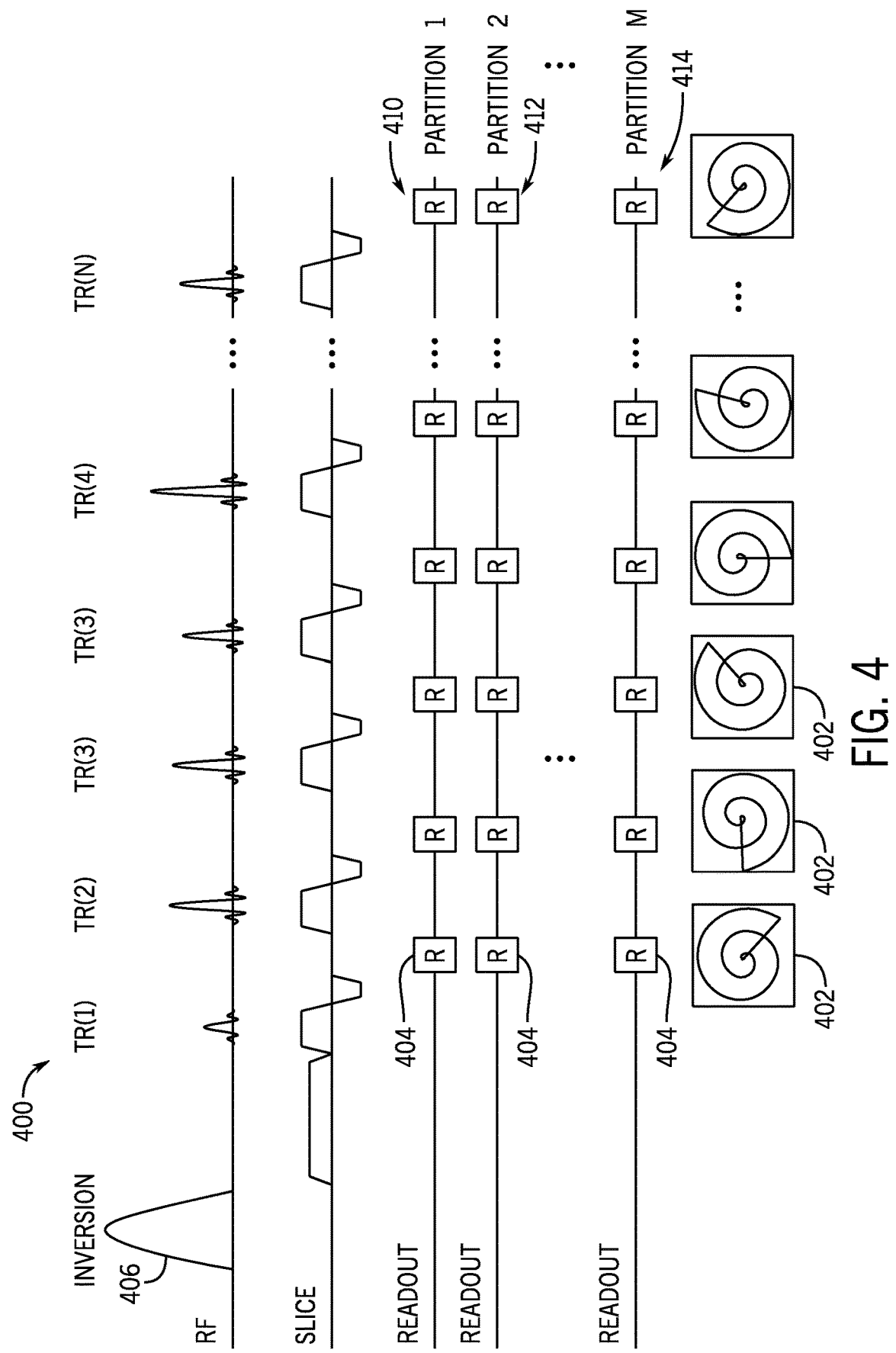
FIG. 4 illustrates an example three-dimensional (3D) FISP pulse sequence in accordance with an embodiment.

FIG. 4 illustrates an example three-dimensional (3D) FISP pulse sequence in accordance with an embodiment. The 3D FISP sequence 400 is similar to the 2D FISP sequence shown in FIG. 3, however, a partition-encoding gradient (not shown) is added to the 3D sequence 400 to enable 3D abdominal imaging. In FIG. 4, the same MRF acquisition pattern, including the flip angles and spiral trajectories, may be used for all partitions 410, 412, 414, which may be acquired sequentially. Similar to the 2D FISP sequence 300 shown in FIG. 3, the 3D FISP sequence 400 shown in FIG. 4 utilizes a spiral MRF acquisition. In the FISP sequence 400, each time point may be acquired with a single spiral arm 402 during an acquisition window R 404 in one TR, which generates an undersampled image. For each 3D MRF measurement, a plurality of time points (e.g., hundreds) may be acquired using continuously varying sequence acquisition parameters such as flip angle and spiral trajectories with a golden-angle order. The FISP sequence 400 contains multiple inversion recovery 406 (e.g., n=3) modules to increase the sensitivity to both the $T_1$ relaxation time. In an embodiment, the FISP sequence 300 may also include $T_2$-preparation modules (not shown), for example, n=6, to increase sensitivity to the $T_2$ relaxation time. In an embodiment, spectrally-selective fat suppression modules (not shown) may also be applied to suppress fat signal.

In another embodiment, a quadratic RF phase-based magnetic resonance fingerprinting (qRF-MRF) pulse sequence may be used to acquire the MRF data at block 204. A qRF-MRF pulse sequence is a balanced steady state free precession (SSFP) based MRF acquisition where the RF phase is varied with a quadratic function resulting in linear sweep and encoding of the on-resonance frequency. For a qRF-MRF acquisition, $T_2^*$ may be mapped via $T_2'$ which is directly associated with frequency dispersion around a center frequency for each voxel. In an embodiment, a wait time may be applied in between each measurement to ensure the transverse magnetization is sufficiently relaxed.

At block 206, the detected PT RF signals (referred to herein as PT navigator signals) are encoded (or embedded) into the acquired MRF data (e.g., via the receiver array). In an embodiment, a PT navigator signal may be encoded in each TR of the MRF acquisition (described above with respect to block 204). The MRF data including the encoded PT navigator signals may be stored in memory or data storage of, for example, the MM system (e.g., MM system 100 shown in FIG. 1) or other computer system. At block 208, the PT navigator signals are extracted from the acquired MRF data. In one embodiment, the PT navigator signals may be extracted by using a one-dimensional (1D) inverse Fourier Transform (FT) performed along the readout direction. The 1D inverse FT performed along the readout direction creates a projection of the data showing a PT index at a single repetition time (TR). The PT navigator signals may be provided by extracting every data point from all of the receiver coils (e.g., in a receiver array of RF system 120 shown in FIG. 1) along the PT index over time for the entire acquisition. In an embodiment, the PT navigator signals may have the dimensions of number of coils (Nc) by total number of PT time points (NPT). The PT navigator signals may be compiled as a function of time. The extracted PT navigator signals may be stored in memory or data storage of, for example, the MRI system (e.g., MM system 100 shown in FIG. 1) or other computer system.

Figure 5:
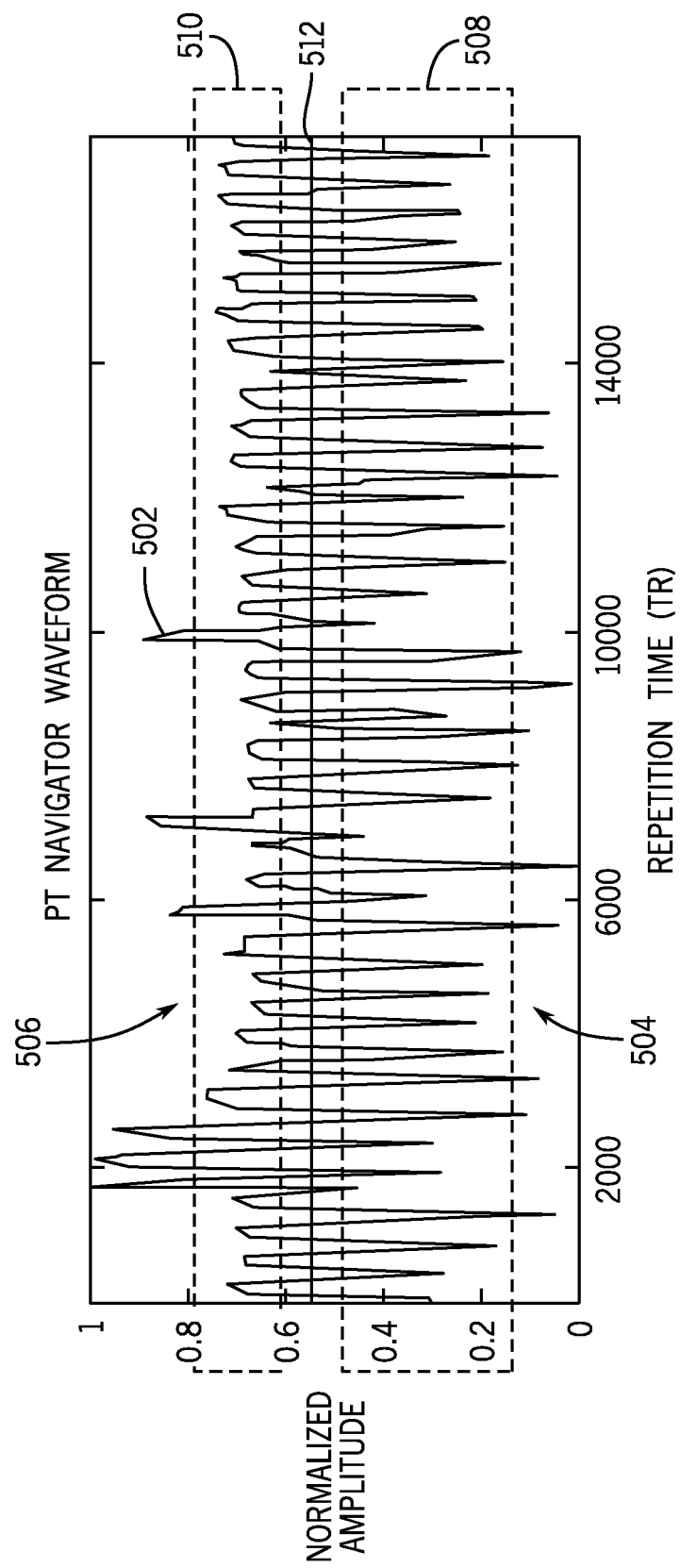
FIG. 5 illustrates an example navigator signal waveform and valid time points for two respiratory states in accordance with an embodiment.

At block 210, a navigator signal waveform is determined using the extracted PT navigator signals from block 208. In an embodiment, principal component analysis (PCA) may be applied to all of the PT navigator signals from all receiver coils. Performing PCA on the PT navigator signals separates out and isolates different components in the PT navigator signals. In an embodiment, the extracted PT navigator signals may be arranged in a chronological order. The component with the most relative power (or energy) within the frequency band of the respiratory motion may be selected as the navigator signal waveform. In an embodiment, the navigator signal waveform may be normalized with respect to its maximum signal level. The navigator signal waveform may be stored in memory or data storage of, for example, the MRI system (e.g., MRI system 100 shown in FIG. 1) or other computer system. The selected navigator signal waveform may be used to generate respiratory state indexes at bock 212. In an embodiment, a respiratory state index is generated for each one of a plurality of selected respiratory states or phases. For example, the respiratory states may be an end-inhalation state and an end-exhalation state. In an embodiment, the respiratory state index for each respiratory state may be generated using thresholding. Each desired respiratory state may be created using the navigator signal waveform by selecting thresholds. FIG. 5 illustrates an example navigator signal waveform and valid time points for two respiratory states in accordance with an embodiment. In the example in FIG. 5, two respiratory states were created using a navigator signal waveform 502 by selecting thresholds for an end-inhalation state 504 and an end-exhalation state 506. A window 508 of accepted time (or data) points defined by the thresholds may be selected for the end-inhalation state 504 and a window 510 of accepted (or valid) data points defined by the thresholds may be selected for the end-exhalation state 506. A mean 512 for the navigator signal waveform 502 is also shown in FIG. 5. The windows 508, 510 of valid data points are then used to obtain a respiratory state index for the end-inhalation state and the end-exhalation state, respectively. For example, the valid data points in each window 308, 310 may be compiled into a respiratory state index for the end-inhalation state and the end-exhalation state, respectively. The respiratory state index for each respiratory state may be stored in memory or data storage of, for example, the MRI system (e.g., MM system 100 shown in FIG. 1) or other computer system.

Returning to FIG. 2a, the respiratory state indexes for each respiratory state are then used to extract a subset of MRF data (referred to herein as respiratory state MRF data) from the acquired MRF data for each respiratory state at block 214. In an embodiment, all of the acquired MRF data may be arranged in a chronological order. Each respiratory state index may be used to identify the acquired MRF data that corresponds to the valid time points for the respiratory state. For the example of two respiratory states as shown in FIG. 3, the respiratory state index for the end-inhalation state may be used to identify the acquired MRF data corresponding to the valid time points for the end-inhalation state. In addition, in this example the respiratory state index for the end-exhalation state may be used to identify the acquired MRF data corresponding to the valid time points for the end-exhalation state. Accordingly, respiratory state MRF data (a subset of the acquired MRF data) is identified for each respiratory state. The respiratory state MRF data for each respiratory state may be stored in memory or data storage of, for example, the MRI system (e.g., MRI system 100 shown in FIG. 1) or other computer system.

In an embodiment where retrospective gating is used and all necessary MRF data is acquired at block 204 using a predetermined number of measurements, the process moves on to block 216 as discussed further below. In an embodiment where prospective gating is used and the MRF data from a single measurement is acquired at block 204, once the respiratory state MRF data subsets of the currently acquired MRF data are generated the process moves to block 236 shown with dotted lines. At block 236, it is determined whether all the necessary MRF data has been acquired, i.e., whether another measurement is needed to acquire missing MRF data. If there is missing MRF data at block 236, the process returns to block 204 and another single measurement or acquisition is performed to acquire MRF data. The process from block 206 to block 212 is repeated for the additional acquired MRF data. At block 214, the additional MRF data is separated into subsets for each respiratory state (using the respiratory state indexes) and combined with the previously acquired MRF data in the appropriate respiratory state MRF data subset to fill in the missing data. Blocks 204 to 214 are repeated until it is determined at block 236 that there is no missing MRF data and all the necessary MRF data has been acquired. When all the necessary MRF data has been acquired at block 236, the process continues with block 216 shown in FIG. 2b.

At block 216, an MRF dictionary is generated that includes known signal evolutions (e.g., simulated signal evolutions). In an embodiment, the MRF dictionary may be generated using a Bloch simulation. The MRF dictionary may be stored in memory or data storage of, for example, the MRI system (e.g., MM system 100 shown in FIG. 1) or other computer system. In another embodiment, the MRF dictionary may already have been generated and is retrieved from memory or data storage. At block 218, a subset of the MRF dictionary (referred to herein as a respiratory state MRF dictionary) is generated for each respiratory state from the MRF dictionary using the respiratory state index corresponding to the respective respiratory state. In an embodiment for an acquisition performed with a qRF-MRF pulse sequence, a partial volume MRF dictionary may be generated for each respiratory state to enable the creation of fat fraction (FF) and water fraction (WF) maps. Each respiratory state MRF dictionary may be stored in memory or data storage of, for example, the MRI system (e.g., MM system 100 shown in FIG. 1) or other computer system. At blocks 220 and 222 (shown with dotted lines), each respiratory state MRF data subset and each respiratory state MRF dictionary, respectively, may optionally be compressed to accelerate reconstruction. The respiratory state MRF data subsets and respiratory state MRF dictionaries may be compressed using a known compression method such as, for example, singular value decomposition (SVD) or randomized SVD (rSVD). For example, a compressed respiratory state MRF dictionary may be generated by applying rSVD to each entry in the respiratory state MRF dictionary. The singular values obtained from applying the rSVD to each dictionary entry are stored as low rank approximations of the true values. The compressed respiratory state MRF data subsets and respiratory state MRF dictionaries may be stored in memory or data storage of, for example, the MRI system (e.g., MRI system 100 shown in FIG. 1) or other computer system.

At block 224, one or more images are reconstructed for each respiratory state using the corresponding respiratory state MRF data subset (or compressed respiratory state MRF data subset). The image(s) may be, for example, an image series for a 2D acquisition or a volume series for a 3D acquisition. In an embodiment, the image(s) may be reconstructed by performing a non-uniform fast Fourier Transform (NUFFT) on a respiratory state MRF data subset. In another embodiment, an iterative low rank reconstruction may also be used to improve image quality and reduce artifacts. The reconstructed image(s) for each respiratory state may be stored in memory or data storage of, for example, the MRI system (e.g., MRI system 100 shown in FIG. 1) or other computer system. At block 226, the respiratory state MRF dictionary for each respiratory state is accessed. As mentioned above, the respiratory state MRF dictionary for each respiratory state may be stored in memory or data storage. At block 228, for each respiratory state the image(s) reconstructed at block 224 are compared to the respiratory state MRF dictionary corresponding to the particular respiratory state to match the reconstructed images with the signal evolutions stored in the respiratory state MRF dictionary. Comparing the reconstructed image(s) to the respiratory state MRF dictionary may be performed in a number of ways such as, for example, using a pattern matching, template matching, or other matching algorithm.

At block 230, for each respiratory state one or more tissue properties of the MRF data and images associated with the respiratory state are determined based on the comparison and matching at block 228. The tissue properties may include, for example, $T_1$, $T_2$, $T_2^*$, $M_0$, fat fraction (FF), water fraction (WF), and off-resonance. The identified tissue properties may be stored in memory or data storage of, for example, the MRI system (e.g., MRI system 100 shown in FIG. 1) or other computer system At block 232, for each respiratory state maps or images may be generated indicating at least one of the identified tissue properties for the tissues in the region of interest in the subject. For example, a map may be generated having a quantitative indication of the at least one tissue property. The maps or images for each respiratory state may be stored in memory or data storage of, for example, the MRI system (e.g., MM system 100 shown in FIG. 1) or other computer system. At block 234, a report may be generated indicating for each respiratory state at least one of the identified tissue properties for the tissue in the region of interest in the subject. For example, the report may include a quantitative indication of the at least one tissue property. The report may include, for example, the images or maps generated at block 232, text or metric based reports, audio reports and the like. The report may be stored in memory or data storage of, for example, the MRI system (e.g., MM system 100 shown in FIG. 1) or other computer system. In addition, the images, maps, or reports may be provided to and displayed on a display (e.g., display 104, 136 or 144 of MEI system 100 shown in FIG. 1).

Computer-executable instructions for free-breathing magnetic resonance fingerprinting (MRF) using a pilot tone (PT) navigator according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly states, are possible and within the scope of the invention.

The invention claimed is:

1. A method for free-breathing abdominal magnetic resonance fingerprinting (MRF), the method comprising:
    applying a pilot tone (PT) radiofrequency (RF) signal in a magnetic resonance imaging (MRI) system environment using a PT RF signal source;
    acquiring, using the MRI system, MRF data from a region of interest in a subject using a free-breathing MRF pulse sequence;
    acquiring, using the MRI system, PT navigator signals based on the applied PT RF signal, wherein the PT navigator signals are associated with a plurality of respiratory states and wherein the PT navigator signals are encoded with the acquired MRF data;
    generating, using a processor, one or more images for each of the plurality of respiratory states based on the MRF data and the PT navigator signals;
    for each respiratory state, comparing the one or more images for the respiratory state to a respiratory state MRF dictionary associated with the respiratory state to determine at least one tissue property of the MRF data associated with the respiratory state; and
    generating at least one quantitative parameter map for the at least one tissue property for each respiratory state.

2. The method according to claim 1, wherein the MRF pulse sequence is a two-dimensional (2D) MRF pulse sequence.

3. The method according to claim 1, wherein the MRF pulse sequence is a three-dimensional (3F) MRF pulse sequence.

4. The method according to claim 1, further comprising generating a respiratory state index for each respiratory state.

5. The method according to claim 4, wherein generating a respiratory state index for each respiratory state comprises:
    extracting the PT navigator signals from the acquired MRF data;
    determining a navigator signal waveform using the extracted PT navigator signals and
    applying one or more thresholds associated with the respiratory state to the navigator signal waveform to identify time points associated with the respiratory state.

6. The method according to claim 4, wherein generating one or more images for each of the plurality of respiratory states based on the MRF data and the PT navigator signals comprises:
    creating a respiratory state MRF data subset for each respiratory state from the acquired MRF data using the respiratory state index,
    reconstructing the one or more images for each respiratory state using the corresponding respiratory state MRF data subset.

7. The method according to claim 1, wherein the respiratory state MRF dictionary associated with each respiratory state is a compressed MRF dictionary.

8. The method according to claim 1, further comprising displaying the at least one quantitative parameter map for the at least one tissue property for each respiratory state on a display.

9. The method according to claim 1, wherein generating one or more images for each of the plurality of respiratory states based on the MRF data and the PT navigator signals comprises retrospective gating.

10. The method according to claim 1, wherein the one or more tissue properties include one or more of $T_1$, $T_2$, $T_2^*$, $M_0$, fat fraction (FF), water fraction (WF), and off-resonance.

11. A system for generating quantitative maps for a region of interest in a subject, the system comprising:
    a pilot tone (PT) radiofrequency (RF) signal source configured to generate a PT RF signal; and
    a magnetic resonance imaging (MRI) system comprising:
        a magnet system configured to generate a polarizing magnetic field about at least a portion of a subject;
        a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals from the subject using a coil array; and a computer system programmed to:
  acquire MRF data from a region of interest in a subject using the MRI system, wherein the MRF data is acquired using a free-breathing MRF pulse sequence;
  acquire PT navigator signals based on the applied PT RF signal using the MRI system, wherein the PT navigator signals are associated with a plurality of respiratory states and wherein the PT navigator signals are encoded with the acquired MRF data
  generate one or more images for each of the plurality of respiratory states based on the MRF data and the PT navigator signals;
  for each respiratory state, compare the one or more images for the respiratory state to a respiratory state MRF dictionary associated with the respiratory state to determine at least one tissue property of the MRF data associated with the respiratory state; and
  generate at least one quantitative parameter map for the at least one tissue property for each respiratory state.

12. The system according to claim 11, further comprising an antenna coupled to the PT RF signal source, the antenna configured to transmit the PT RF signal in an environment of the MRI system.

13. The system according to claim 11, wherein the MRF pulse sequence is a two-dimensional (2D) MRF pulse sequence.

14. The system according to claim 11, wherein the MRF pulse sequence is a three-dimensional (3F) MRF pulse sequence.

15. The system according to claim 11, wherein the computer system is further programmed to generate a respiratory state index for each respiratory state.

16. The system according to claim 11, wherein the respiratory state MRF dictionary associated with each respiratory state is a compressed MRF dictionary.

17. The system according to claim 11, wherein the computer system is further programmed to generate the one or more images for each of the plurality of respiratory states using retrospective gating.

18. The system according to claim 11, wherein the one or more tissue properties include one or more of $T_1$, $T_2$, $T_2^*$, $M_0$, fat fraction (FF), water fraction (WF), and off-resonance.

19. The system according to claim 11, wherein the computer system is further programmed to extract the PT navigator signals from the acquired MRF data.

20. The system according to claim 11, wherein the region of interest is an abdominal region.

* * * * *